United States Patent
Filippi et al.

(10) Patent No.: US 8,039,519 B2
(45) Date of Patent: Oct. 18, 2011

(54) PROCESS AND PLANT FOR SUBSTITUTE NATURAL GAS

(75) Inventors: Ermanno Filippi, Castagnola (CH); Francesco Baratto, Como (IT)

(73) Assignee: Methanol Casale S.A. (CH)

( * ) Notice: Subject to any disclaimer, the term of this patent is extended or adjusted under 35 U.S.C. 154(b) by 33 days.

(21) Appl. No.: 12/415,556

(22) Filed: Mar. 31, 2009

(65) Prior Publication Data

US 2009/0264542 A1 Oct. 22, 2009

(30) Foreign Application Priority Data

Apr. 16, 2008 (EP) .................................... 08007452

(51) Int. Cl.
*C07C 27/00* (2006.01)
(52) U.S. Cl. ........................................ 518/706; 518/705
(58) Field of Classification Search .................. 518/700, 518/705, 706

See application file for complete search history.

(56) References Cited

U.S. PATENT DOCUMENTS

| | | | |
|---|---|---|---|
| 3,854,895 A | 12/1974 | Muller | |
| 3,970,435 A | 7/1976 | Schultz et al. | |
| 4,005,996 A | 2/1977 | Hausberger et al. | |
| 4,064,156 A | 12/1977 | McRobbie | |
| 4,133,825 A | 1/1979 | Stroud et al. | |

FOREIGN PATENT DOCUMENTS

GB 2060686 A 5/1981

OTHER PUBLICATIONS

Mozaffarian, M. et al. "Feasibility of Biomass/Waste-Related SNG Production Technologies", Energy Research Center of the Netherlands, ECN Report ECN-C—03-066, Jul. 2003, pp. 1-117.

*Primary Examiner* — Jafar Parsa
(74) *Attorney, Agent, or Firm* — Akerman Senterfitt

(57) ABSTRACT

A process for producing substitute natural gas (SNG) comprising the steps of reacting a fresh syngas (11) into a methanation section (10) comprising adiabatic reactors (101-104) connected in series, with heat removal and reacted gas-recirculation, wherein the fresh syngas is fed in parallel to said adiabatic reactors. In a preferred embodiment the reacted gas is recirculated to the first reactor (101) and further dilution of the fresh gas at the inlet of the first and second reactor is achieved by steam addition.

8 Claims, 1 Drawing Sheet

PROCESS AND PLANT FOR SUBSTITUTE NATURAL GAS

FIELD OF THE INVENTION

The invention relates to a process for producing substitute natural gas (SNG). The invention, in particular, relates to a process for producing SNG by reacting a synthesis gas comprising hydrogen and carbon oxides in a methanation section comprising adiabatic reactors with intermediate heat recovery and gas recirculation. The invention also relates to a plant operating with such process.

PRIOR ART

Interest in the technical field of SNG production is continuously rising. SNG is a clean fuel which can be distributed with existing natural gas pipelines and facilities, and can be used as a substitute of natural gas in a wide range of applications.

A known process to produce substitute natural gas (SNG) involves methanation of a synthesis gas (make-up syngas) comprising hydrogen and carbon oxides. By the reaction of methanation, the make-up syngas is converted in a more valuable product consisting of 95% or more of methane (CH4) with small amounts of carbon dioxide, hydrogen and inerts. The syngas may be obtained from coal or biomass gasification with further advantages: SNG from coal gasification is attractive because of large availability of coal, while SNG from biomass gasification gives no contribution to the CO2 global emissions compared to fossil fuels.

Basically, the process of methanation of the syngas involves the following, strongly exothermal reactions:

  (I)

  (II)

where reaction (I) has a thermal output (enthalpy of reaction) of around 206 kJ/mol and reaction (II) of around 165 kJ/mol.

According to known art, the above reactions are carried out in a so-called methanation section comprising a plurality of adiabatic reactors with heat recovery and gas recirculation.

The reactors are disposed to operate in series, i.e. the fresh gas is fed to the first reactor and each of the subsequent reactors is fed with a partially-converted gas stream taken from the previous (upstream) reactor of the section. The reactors contain an appropriate catalyst to increase the yield of the reaction.

Heat recovery and gas recirculation are used to keep the exothermal reactions under control and avoid an excessive temperature inside reactors, that may damage the reactor itself and/or the catalyst. More in detail, heat recovery is provided by heat exchangers cooling the hot gas stream at the outlet of each reactor e.g. by producing high pressure steam. Recirculation is a further measure to control the reaction rate and the temperature inside the reactors, by dilution of the fresh syngas fed to the first reactor with a portion of the reacted gas. The gas recirculation requires the provision of an appropriate compressor.

For example, a well known process marketed under the name TREMP™ involves a methanation section comprising a first reactor fed with fresh syngas having appropriate hydrogen to carbon monoxide ratio, and two further reactors. Reacted gas at the output of the first reactor passes through a super heater and a high pressure boiler and is split into two streams. One stream is directed to the second reactor, and the other stream is recirculated to the inlet of the first reactor via a gas preheater and a compressor. In another known process, a recirculation gas flow is taken downstream a second or subsequent reactor, and mixed with the fresh gas fed to the first reactor, i.e. the recirculation loop comprises all the reactors of the methanation section, with the possible exception of the last (finishing) reactor.

A common feature of the prior-art processes is that the fresh gas input is entirely directed to the first reactor. Due to relevant heat output of the reaction, a strong dilution is required and, hence, a relevant portion of the reacted gas need to be re-circulated. The ratio between the total molar flow rate entering the first reactor and the molar flow rate of the fresh syngas feedstock can reach a value up to 6 or 7, meaning that about 15-20% or even less of the gas entering the first reactor is fresh syngas, while 80% or more is re-circulated reacted gas.

As a consequence, the power absorption of the compressor for gas recirculation is quite high and hence the compressor itself is a large and expensive item. Another drawback is that the amount of re-circulated gas increases the flow rate through the reactors, especially the first one, requiring larger and more expensive units and a larger quantity of catalyst.

All these drawbacks affect the cost of the methanation section and then the competitiveness of the price of the SNG over the fossil natural gas; on the other hand, the above high value of re-circulation ratio appears indispensable in the prior art to avoid overheat of the reactors.

SUMMARY OF THE INVENTION

The problem underlying the invention is to provide a more cost-effective and competitive process for converting a syngas containing carbon oxides and hydrogen into substitute natural gas. More in detail, the invention aims to reduce the need of gas recirculation and related drawbacks still affecting the prior-art processes.

The basic idea of the invention is to feed the fresh make-up syngas in parallel to the reactors of the methanation section. Hence, the above problem is solved with a process for producing SNG from a fresh syngas feedstock, said process comprising the steps of reacting said fresh syngas into a methanation section comprising at least a first adiabatic reactor and further adiabatic reactor(s) connected in series, so that each of said further reactor(s) is fed with a gas stream taken from the previous reactor of the methanation section, and recirculating at least part of the reacted gas as input gas of at least one of said reactors, characterized in that said fresh syngas feedstock is fed in parallel to said reactors.

In a preferred embodiment, the fresh make-up syngas feedstock is split into a plurality of fresh gas streams and each of said fresh gas streams is fed to a respective one of said reactors of the methanation section. More preferably, each of said fresh gas streams is between 15% and 35% of the total available syngas.

Typical arrangement is with four main reactors in series with the fresh make-up gas split 25% to the first reactor, 20% to the second, 25% to the third and 30% to the fourth. The number of reactors depends on the type of catalyst that is used (allowable maximum outlet temperature) and the quality of gas that is required (maximum amount of $CO_2$ and $H_2$).

According to another aspect of the invention, gas recirculation is carried out by taking a portion of the gas stream at the outlet of the first reactor and feeding said gas portion to the same first reactor. In other words, according to said further aspect of the invention the gas recirculation loop involves the first reactor only, which is fed with fresh syngas added with re-circulated reacted gas, while each of the second and further reactors is fed with fresh syngas added with the reacted gas coming from the previous reactor of the methanation section.

According to other aspects of the invention, steam is added at the inlet of at least the first reactor, and preferably also at the inlet of the second reactor of the methanation section. Steam addition is effective in controlling the reaction temperature because the steam dilute the fresh syngas and shifts the chemical equilibrium reducing the reaction rate inside the reactors, being one of the products of reactions (I) and (II).

In a preferred embodiment, reacted gas from the first reactor is split into a first gas portion and a second gas portion; said first gas portion is re-circulated to dilute the fresh gas stream led to the first reactor, obtaining a diluted gas stream at the inlet of said first reactor which is further diluted by addition of a steam flow before entering the first reactor; said second gas portion is used to dilute the fresh gas fed to a second reactor of the methanation section, and also the gas flow entering said second reactor is further diluted with steam. Steam can be added before of after dilution of the fresh gas with the re-circulated or reacted gas.

An object of the invention is also a methanation section for converting a syngas containing carbon oxides and hydrogen into substitute natural gas, operating with the above process, and a plant comprising such methanation section.

In one embodiment of the invention, the methanation section comprises a first reactor and a plurality of further reactors adapted to carry out methanation of said fresh syngas, and a fresh syngas feeding line is arranged to feed said fresh syngas in parallel to said first and further reactors, each reactor receiving a predetermined portion of the fresh syngas.

In a preferred embodiment, there is provided a re-circulation loop receiving a portion of reacted gas taken from the first reactor, and mixing said portion of reacted gas with the fresh syngas feeding portion of the first reactor. More preferably, steam addition lines are provided to further dilute the gas entering the first and second reactor of the methanation section.

The invention has the following advantages. As the first reactor receives only a portion of the fresh gas feedstock, the temperature inside can be controlled with a lower gas recirculation compared to prior art, e.g. with total to fresh gas molar ratio ~2. The need of re-circulating the reacted gas is further decreased by the steam addition of preferred embodiments of the invention. Each of the second and further reactors receives a portion of the fresh gas diluted with the partially converted gas coming from the upstream reactor of the methanation section, so that there is no need to provide gas recirculation also to said reactors.

Thanks to the invention, the compressor of the recirculation loop is much smaller than the compressor required in the prior art. For example a plant operating with a prior-art process and capable of 2·10^6 Nm³/day of SNG typically requires a 8-MW compressor for gas recirculation, while a plant operating with the inventive process and capable of the same output would requires a much less expensive 350-kW compressor.

A further advantage is that due the partition of the fresh gas and the reduced gas recirculation, there is a less flow rate through the reactors of the methanation section and especially at the inlet of the first compressor. Hence, the invention allows to use smaller units and a less quantity of catalyst is required for each reactor.

It is to be noted that the heat recovery is not affected by the invention, i.e. the production of high pressure superheated steam is the same as a prior-art process.

All the above advantages make the SNG more competitive over fossil natural gas or other fuels. The invention is particularly useful to produce SNG from biomass or coal gasification.

The features and advantages of the present invention will be more evident from the following description of preferred indicative and non-limiting embodiment examples, with reference to the attached FIGURE.

DETAILED DESCRIPTION OF A PREFERRED EMBODIMENT

Figure 1:
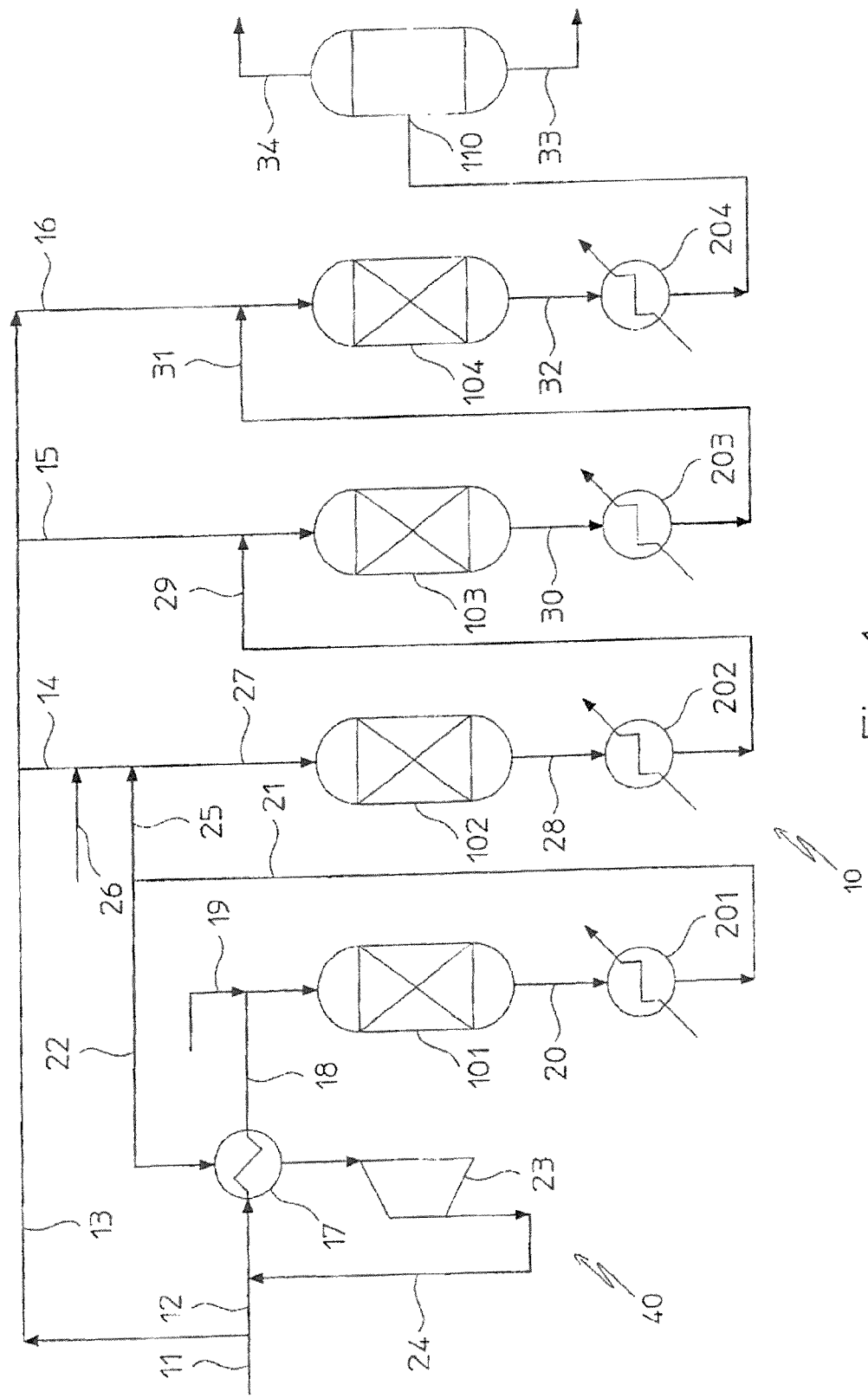
FIG. 1 is a schematic layout of a plant operating with the inventive process.

With reference to FIG. 1, a methanation section for SNG production is globally indicated as 10, and receives a feedstock 11 of a fresh syngas containing carbon oxides and hydrogen. Said fresh syngas stream 11 can be obtained for example in a coal or biomass gasification section (not shown).

The methanation section 10 comprises a series of adiabatic reactors 101-104 with recovery heat exchangers 201-204. Reactors 101 to 104 are per se known, for example axial or axial-radial flow reactors with an appropriate catalyst, operating at around 35 bar pressure with inlet gas temperature between 240 and 300° C. and outlet gas temperature around 600° C. Heat exchangers 201 to 204 receive the hot gas from reactors 101 to 104, respectively, and may operate as HP steam boilers or provide water pre-heating or steam superheating, according to the needs. Hot water/steam line of exchangers 201 to 204 is not shown in the FIGURE for simplicity.

Syngas stream 11 is fed in parallel to reactors 101 to 104, as shown. The syngas feeding line of the methanation section 10 provides a split of the stream 11 into a feeding stream 12 directed to the first reactor 101 and a feeding stream 13 which is further partitioned into feeding lines 14, 15 and 16 directed to reactors 102, 103 and 104 respectively. Preferably, each of said gas streams 12 to 16 is between 15 an 35% molar flow rate of total syngas feedstock 11.

The gas stream 12, before entering the first reactor 101, is diluted with re-circulated gas stream 24 and fed to a preheater 17. The resulting diluted and preheated stream 18 is added in the example with steam from line 19 to further dilute the fresh syngas, and then introduced into the reactor 101.

Output gas stream 20 from the reactor. 101, which is partially converted into methane and has a high temperature, e.g. 600° C., as a result of the exothermal methanation reactions, is cooled in the heat exchanger 201 obtaining a cooled reacted gas stream 21.

A first portion 22 of said cooled gas stream 21 is re-circulated to the reactor 101 via a recirculation loop 40 comprising a compressor 23. More in detail, the gas stream 22 is passed through pre-heater 17 to preheat the gas stream entering the reactor 101, and fed to the compressor 23. The re-circulated gas stream 24 delivered by compressor 23, as stated above, is used to dilute the fresh syngas portion 12 directed to the reactor 101.

Preferably, the ratio between the total flow of stream 18 entering the first reactor 101, and the fresh gas fed to the same reactor 101 via gas stream 12, is around 2 mol/mol.

A second portion 25 of the first reactor output stream 21 is mixed with the fresh make-up gas stream 14, and further added with steam via line 26, thus obtaining a diluted feeding gas stream 27 of the second reactor 102. Outlet gas stream 28 of said second reactor 102 is cooled in the heat exchanger 202 and the cooled gas stream 29 is fed to the third reactor 103 together with the fresh gas stream 15. In a similar way, cooled gas stream 30 from reactor 103 is mixed with the fresh gas 16 and fed to fourth reactor 104.

It should be noted that steam can be added before of after dilution of the fresh gas with the re-circulated or reacted gas. Preferably steam 19 is added to the diluted and preheated flow 18, as shown; steam 26 can be added to fresh gas 14 or to fresh gas 14 diluted with the reacted gas portion 25.

Outlet 32 of fourth reactor 104 is cooled in the heat exchanger 204 and sent to a separator 110 obtaining a SNG stream 34 and a condensate 33; the SNG stream 34 may be directed to a further, so-called finishing reactor. Removing the condensate 33 before feeding the SNG to the finishing reactor is preferred in order to have a more valuable final product.

The SNG typically is composed of 95% or more of methane (CH4) with small percentages of carbon dioxide, hydrogen and inerts. The SNG obtained can be used for any purpose.

A detailed example is now disclosed. In a methanation section 10, as shown in FIG. 1, 435.000 Nm$^3$/h of make up gas@ 37° C. are fed at 11, and a flow 12 of 109.000 Nm$^3$/h is fed to first reactor 101. The remaining part is divided into 88.000, 111.000 and 127.000 Nm$^3$/h respectively to reactors 102, 103 and 104. A flow of 35.000 kg/h of steam @ 450° C. is added at 19 and a 20.000 kg/h of steam at the same temperature are added at 26, while 117.400 Nm$^3$/h of steam-diluted syngas are recycled at 22 and merged with make-up gas 12 via line 24. Around 230.000 Nm$^3$/h of SNG are obtained at stream 34. Temperature at the outlet of reactors is around 600° C.

The methanation section 10 can be a subsection of a plant for producing SNG from a suitable source, e.g. coal or biomass, said plant including further subsections like a gasifier, air separation unit (ASU), CO shift converter to provide appropriate ratio between hydrogen and CO content of the syngas, acid gas removal, and so on. It should be noted that particulars of the methanation section 10 such as valves, pumps, auxiliaries. etc. are not shown as they are well known to the skilled person.

The invention claimed is:

1. A process for producing SNG from a fresh syngas feedstock, said process comprising at least the steps of:
   reacting said fresh syngas into a methanation section comprising at least a first adiabatic reactor and at least one further adiabatic reactor connected in series, so that each of said at least one further reactor(s) is fed with a gas stream taken from the previous reactor of the methanation section;
   feeding said fresh syngas feedstock in parallel to each of said reactors; and
   re-circulating at least a portion of the reacted gas as input gas to at least one of said reactors, wherein at least a portion of a reacted gas stream taken from said first reactor is used as a re-circulated gas to dilute the fresh syngas feedstock stream fed to said first reactor, obtaining a diluted gas stream at the inlet of said first reactor.

2. The process according to claim 1, wherein said fresh syngas feedstock is split into a plurality of fresh gas streams, each of said fresh gas streams being fed to a respective one of said reactors.

3. The process according to claim 2, wherein said methanation section comprises a plurality of said further adiabatic reactors and each of said fresh gas streams is between 15% and 35% molar of the total gas feedstock.

4. The process according to claim 1, wherein said portion of reacted gas stream is fed to the inlet of the first reactor via a re-circulation loop comprising a compressor for the re-circulated gas stream and a pre-heater for heating said diluted gas stream before entering the first reactor.

5. The process according to claim 1, wherein the molar ratio between the total diluted gas flow entering the first reactor, and the fresh gas stream fed to said first reactor is around 2.

6. The process according to claim 1, wherein steam is added at the inlet of at least the first reactor to further dilute the inlet gas.

7. The process according to claim 6, wherein reacted gas from the first reactor is split into a first gas portion and a second gas portion;
   said first gas portion is re-circulated to dilute the fresh gas stream fed to said first reactor, obtaining a diluted gas stream at the inlet of said first reactor;
   said diluted gas stream is further diluted by addition of a steam flow before entering the first reactor;
   said second gas portion is used to dilute fresh gas fed to a second reactor of the methanation section and the gas flow entering said second reactor is further diluted with steam.

8. The process of according to claim 1, wherein said reactors operate at around 35 bar pressure.

* * * * *